US006175092B1

United States Patent
Binette et al.

(10) Patent No.: US 6,175,092 B1
(45) Date of Patent: Jan. 16, 2001

(54) METHOD AND APPARATUS FOR CLASSIFYING BATCHES OF WOOD CHIPS OR THE LIKE

(75) Inventors: Sylvain Binette, Saint-Louis de France; Jacques Labbé, Sainte-Foy; Pierre Bédard, Charlesbourg; Jean-Pierre Couturier, Sainte-Foy, all of (CA)

(73) Assignee: Centre de Recherche Industrielle du Québec, Sainte-Foy (CA)

( * ) Notice: Under 35 U.S.C. 154(b), the term of this patent shall be extended for 0 days.

(21) Appl. No.: 09/163,338

(22) Filed: Sep. 30, 1998

(30) Foreign Application Priority Data

Jan. 23, 1998 (CA) .................................. 2228023

(51) Int. Cl.⁷ ................................. B07C 5/00; G01J 5/02
(52) U.S. Cl. ...................... 209/587; 209/938; 250/339.1; 250/341.8
(58) Field of Search .................................. 209/517, 518, 209/576, 577, 580, 581, 587, 938; 250/341.8, 910, 339.1; 356/402, 407, 425

(56) References Cited

U.S. PATENT DOCUMENTS

| 3,794,843 | * | 2/1974 | Chen ........................... 250/359 |
| 4,992,949 | | 2/1991 | Arden . |
| 5,006,225 | * | 4/1991 | Beauchemin et al. ........... 209/518 X |
| 5,274,244 | * | 12/1993 | Johansson et al. ............. 250/563 |
| 5,440,127 | * | 8/1995 | Squyres ........................ 250/341.8 |
| 5,818,594 | * | 10/1998 | Lukander ...................... 356/376 |

FOREIGN PATENT DOCUMENTS

| 4202168 | | 1/1992 | (DE) . |
| 4137008 | * | 5/1993 | (DE) ........................ 209/587 |
| WO 94/28397 | | 5/1994 | (WO) . |
| WO 94/25838 | | 11/1994 | (WO) . |

* cited by examiner

Primary Examiner—Tuan N. Nguyen
(74) Attorney, Agent, or Firm—Swabey Ogilvy Renault (57) ABSTRACT

A method and apparatus for classifying batches of wood chips or the like according to light reflection characteristics; provide optimal use of darker wood chips in pulp and paper processes. According to a preferred embodiment, light produced by a set of illumination sources is evenly directed onto superficial wood chips of an inspected batch portion transported on a conveyor while being inspected by a camera disposed over the conveyor. The superficial wood chips presenting light reflection characteristics being substantially representative of the wood chips of the inspected batch, reflected light is sensed by the camera to produce electrical signals representing rejection intensity values for the wood chips of the batch portion. From the electrical signals produced, image processing is performed to provide global reflection intensity data for the inspected batch, which are then compared with reference reflection intensity data to provide classification of the inspected wood chips batch into proper wood chips grade according to its light reflection characteristics.

24 Claims, 6 Drawing Sheets

METHOD AND APPARATUS FOR CLASSIFYING BATCHES OF WOOD CHIPS OR THE LIKE

FIELD OF THE INVENTION

The present invention relates to classification of batches of wood chips or the like, and more particularly to a method and apparatus for classifying batches of wood chips according to light reflection characteristics.

BACKGROUND OF THE INVENTION

In the past years, significant efforts have been devoted to develop processes for the production of pulp and paper products aimed at reducing manufacturing costs while improving product quality. Quality control of the raw materials entering in the production of pulp and paper products, particularly regarding wood chips used, has been identified as a key factor in process optimization.

A known approach to control quality of wood chips consists in treating wood chips at the manufacturing stage. Such an approach is employed in the wood chips manufacturing method disclosed in U.S. Pat. No. 5,577,671 issued on Nov. 26, 1996 to Seppanen et al, which method consists of separating from ground whole-tree chips, bark and cellulose wood chips through a series of separation stages including pneumatic separation, vibration segregation with sieve and color difference sorting. The resulting low bark, pale wood chips can be then processed using a minimum quantity of bleaching agent. Although processing cost can be minimized accordingly, added manufacturing cost due to bark separation step may still maintain overall production cost high.

Another known approach consists of sorting trees according to their types prior to wood chips manufacturing, to produce corresponding batches of wood chips presenting desired characteristics associated with these types. Typically, hardwood trees such as poplar, birch and maple are known to generally produce pale wood chips while conifers such as pine, fir and spruce are known to generally yield darker wood chips. In practice, wood chips batches can either be produced from trees of a same type or from a blend of wood chips made from trees of plural types, preferably of a common category, i.e., hardwood trees or conifers, to seek wood chips uniformity. However, chips characteristics basically depending on initial bark content of wood chips used, knowledge of the types of wood chips for a given batch does not necessarily give a reliable indication of the chips quality.

SUMMARY OF INVENTION

It is therefore an object of the present invention to provide a method and apparatus for classifying batches of wood chips or the like according to optical characteristics representative of chips quality or grade.

According to the above object, from a broad aspect of the present invention, there is provided a method for classifying batches of wood chips or the like according to light reflection characteristics, comprising the steps of: a) directing light onto superficial wood chips included in at least a representative portion of an inspected one of said wood chips batches, said superficial wood chips presenting light reflection characteristics being substantially representative of the wood chips of the inspected batch; b) sensing light reflected on the superficial wood chips included in said batch portion to produce electrical signals representing reflection intensity values for the superficial wood chips included in said batch portion; c) deriving from the electrical signals global reflection intensity data characterizing the inspected batch of wood chips; and e) comparing the global reflection intensity data with reference reflection intensity data to provide classification of said inspected batch of wood chips according its light reflection characteristics.

According to a further broad aspect of the present invention, the method comprises the steps of: a) directing light orto superficial wood chips included in at least a representative portion of an inspected one of said wood chips batches, said superficial wood chips presenting light reflection characteristics being substantially representative of the wood chips of the inspected batch; b) sensing light reflected on the superficial wood chips included in said batch portion to produce first electrical signals representing reflection intensity values for the superficial wood chips included in said batch portion; c) measuring moisture of said superficial wood chips to produce second electrical signals representing average moisture values for the superficial wood chips included in said batch portion; d) deriving from said first and second electrical signals global reflection intensity data characterizing the inspected batch of wood chips, said global reflection intensity data being normalized according to a predetermined moisture reference value; and e) comparing the global reflection intensity data with reference reflection intensity data to provide classification of said inspected batch of wood chips according its light reflection characteristics.

According to a still further broad aspect of the present invention, there is provided an apparatus for classifying batches of wood chips or the like according to light reflection characteristics. The apparatus comprises illumination means for directing light onto superficial wood chips included in at least a representative portion of an inspected one of said wood chips batches, said superficial wood chips presenting light reflection characteristics being substantially representative of the wood chips of the inspected batch. The apparatus further comprises image creating means for sensing light reflected on the superficial wood chips included in said batch portion to produce image electrical signals representing reflection intensity values for the wood chips included in said batch portion. The apparatus further comprises means for deriving from the image electrical signals global reflection intensity data for the inspected batch; and means for comparing the global reflection intensity data with reference reflection intensity data to provide classification of said inspected batch of wood chips according its light reflection characteristics.

According to a still further broad aspect of the present invention, the apparatus comprises illumination means for directing light onto superficial wood chips included in at least a representative portion of an inspected one of said wood chips batches, said superficial wood chips presenting light reflection characteristics being substantially representative of the wood chips of the inspected batch, image creating means for sensing light reflected on the superficial wood chips included in said batch portion to produce first electrical signals representing reflection intensity values for the wood chips included in said batch portion, and moisture detector means for producing second electrical signals representing average moisture values for the superficial wood chips included in said batch portion. The apparatus further comprises means for deriving from said first and second electrical signals global reflection intensity data for the inspected batch, said global reflection intensity data being normalized according to a predetermined moisture reference value and means for comparing the global reflection intensity data with reference reflection intensity data to provide classification of said inspected batch of wood chips according its light reflection characteristics.

According to a preferred embodiment of the present invention, a method and apparatus for classifying batches of wood chips or the like according to optical characteristics is provided, which allow optimal use of darker wood chips in pulp and paper processes. Although hardwood wood chips generally require more bleaching agent when being processed, their cellulose fibers may exhibit better physical characteristics than fibers found in conifers for the purpose of producing products presenting particular structural characteristics. Therefore, mixing a relatively small batch of such darker wood chips with a large batch of pale wood chips can produce a blend presenting the quality required for optimal processing, provided the characteristics of the darker wood chips batch have been accurately determined, to adjust parameters of the process accordingly.

BRIEF DESCRIPTION OF THE DRAWINGS

A preferred embodiment of the present invention will now be described in detail with reference to the accompanying drawings in which.

DETAILED DESCRIPTION OF THE PREFERRED EMBODIMENTS

Figure 1:
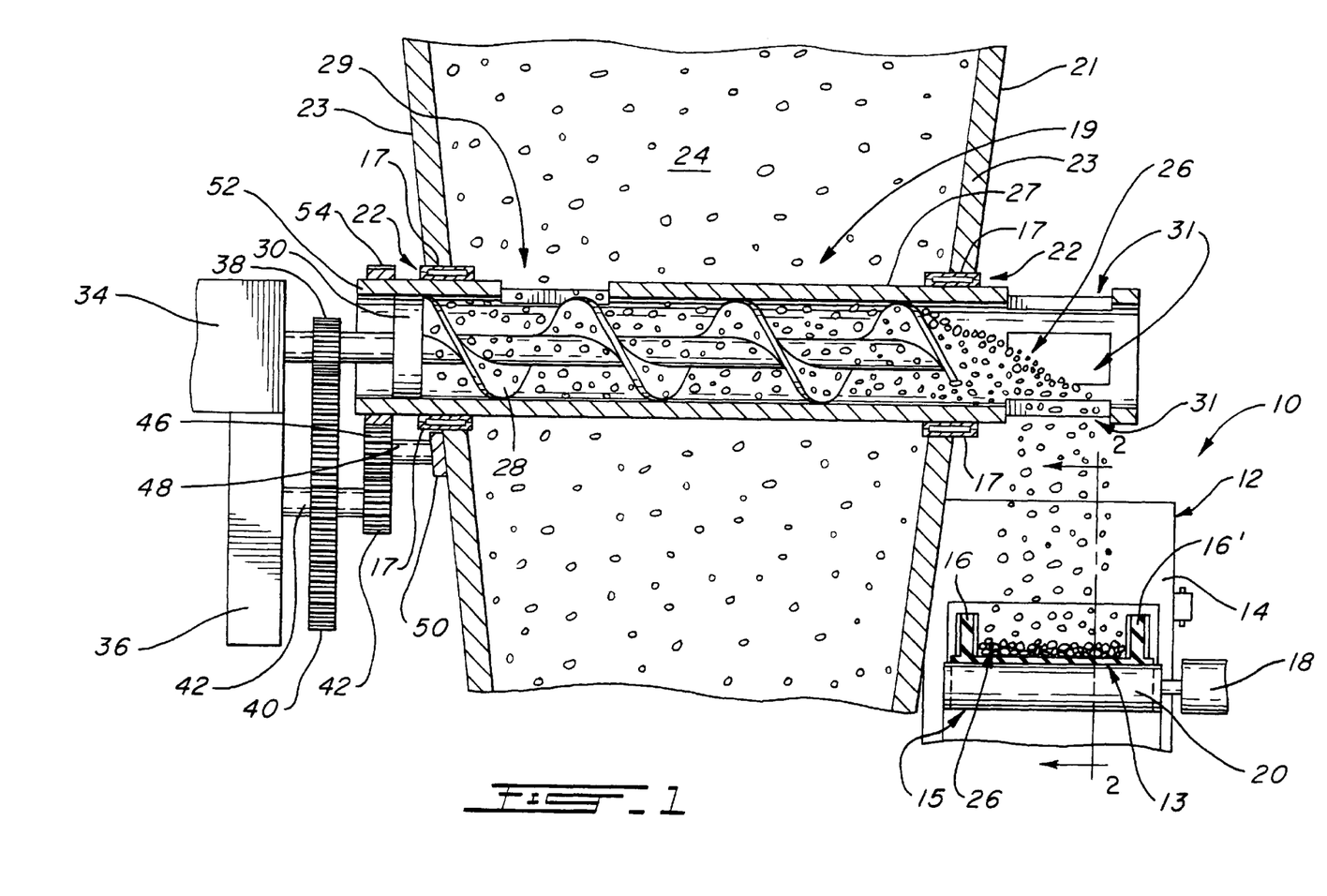
FIG. 1 is a partially cross-sectional end view of a receiving hopper provided with a sampling screw feeding a conveyor transporting wood chips through an inspection station according to the preferred embodiment of the present invention.

Referring now to FIG. 1, an apparatus according to the preferred embodiment of the present invention is generally designated at 10, which includes an inspection station 12 comprising an enclosure 14 through which extends a powered conveyor 15 coupled to a drive motor 18. The conveyor 15 is preferably of a trough type having a belt 13 defining a pair of opposed lateral extensible guards 16, 16' of a known design, for keeping the material to be inspected on the conveyor 15. Adjacent an input end 29 of the conveyor 15 is an hopper 21 for receiving at an upper inlet thereof (not shown) a batch 24 of material to be inspected for classification purposes, which material essentially consists of wood chips 26 in the example shown. However, it is to be understood that batches of other similar wooden materials could be advantageously classified in accordance with the present invention, such as flakes, shavings, slivers, splinters and shredded wood. Typically, the wood chips 26 may be caused to flow under gravity and discharged through a controlled outlet (not shown) provided at the bottom part of the upper 21 for further processing. Radially extending through a pair of opposed openings 22 receiving rotary bearings 17 provided on the peripheral wall 23 of the hopper 21 is a sampling device 19 having an elongated cylindrical sleeve 27 of a circular cross-section adapted to receive for rotation therein a feeding screw 28 of a known construction. The sleeve 27 has a lateral input opening 29 allowing wood chips 26 to cyclically reach an input portion of the screw 28 whenever the sleeve opening 29 passes through an upper position as shown in FIG. 1. The sleeve 27 further has one or more output openings 31 generally disposed over the conveyer input end 29 to allow substantially uniform discharge of the sampled wood chips 26 on the conveyer belt 13. The feeding screw 28 has a base disk 30 being coupled to the driven end of a driving shaft 32 extending from a drive motor 34 mounted on a support frame 36, which motor 34 imparts rotation to the screw 28 at a given RPM. The driving shaft 32 is provided with a small driving gear 38 cooperating with a large gear 40 and a small gear 42 mounted on first idle shaft 44 supported by base 36, to transmit driving couple at a lower RPM to a reversing gear 46 mounted on a second idle shaft 48 rotatably engaging a support member 50 rigidly secured to the outer surface of hopper 21. The sleeve 27 has a driven end 52 provided with an outer annular disk 54 having radially extending gear teeth cooperating with the reversing gear 46 to impart rotation to the sleeve in a direction opposed to clockwise rotation of screw 28 and at a lower RPM, as will be explained later in more detail.

Figure 2:
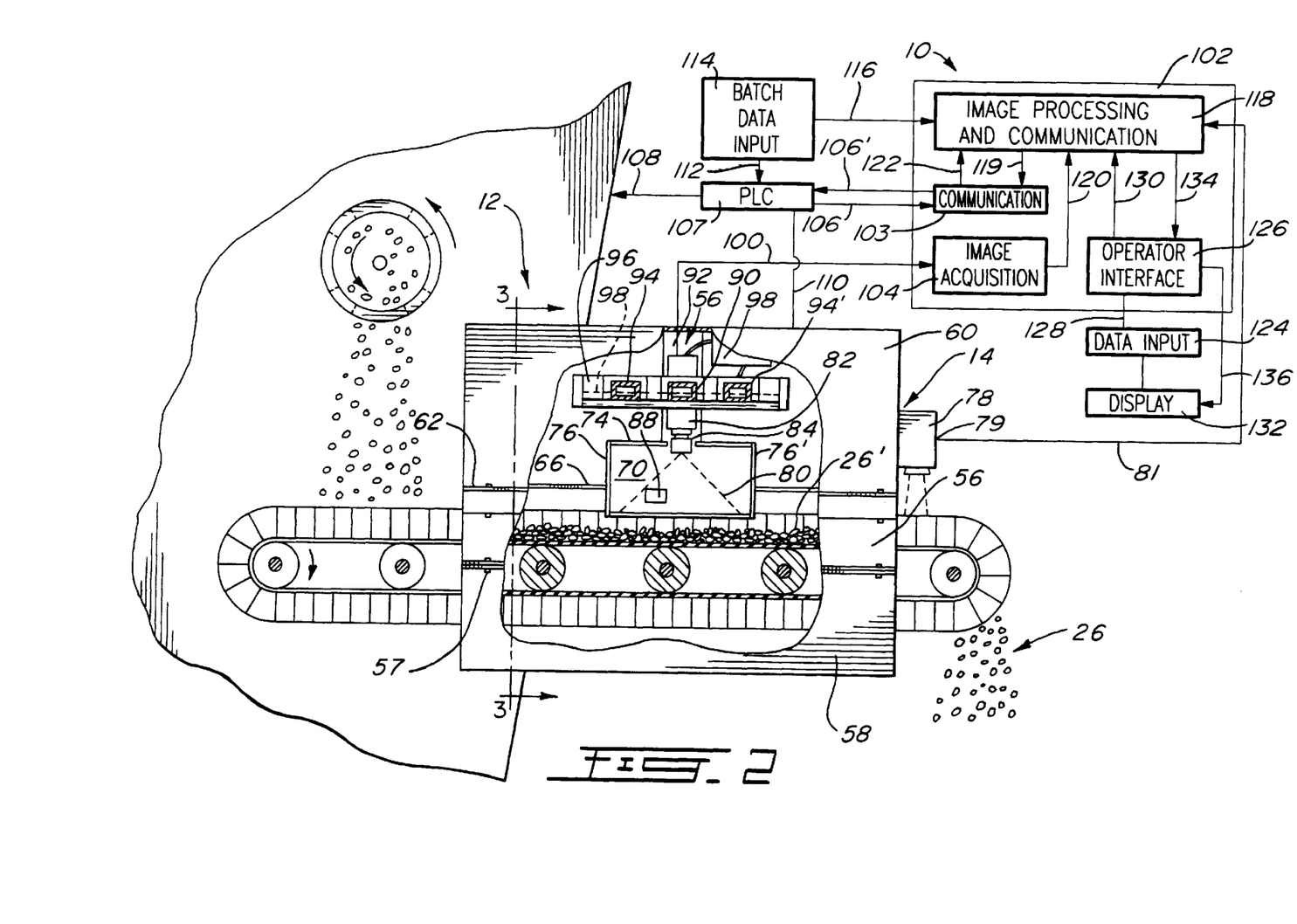
FIG. 2 is a partially cross-sectional side view along section line 2—2 of the inspection station shown in FIG. 1 and being connected with a computer unit shown in block diagram and according to the preferred embodiment of the invention.
Figure 3:
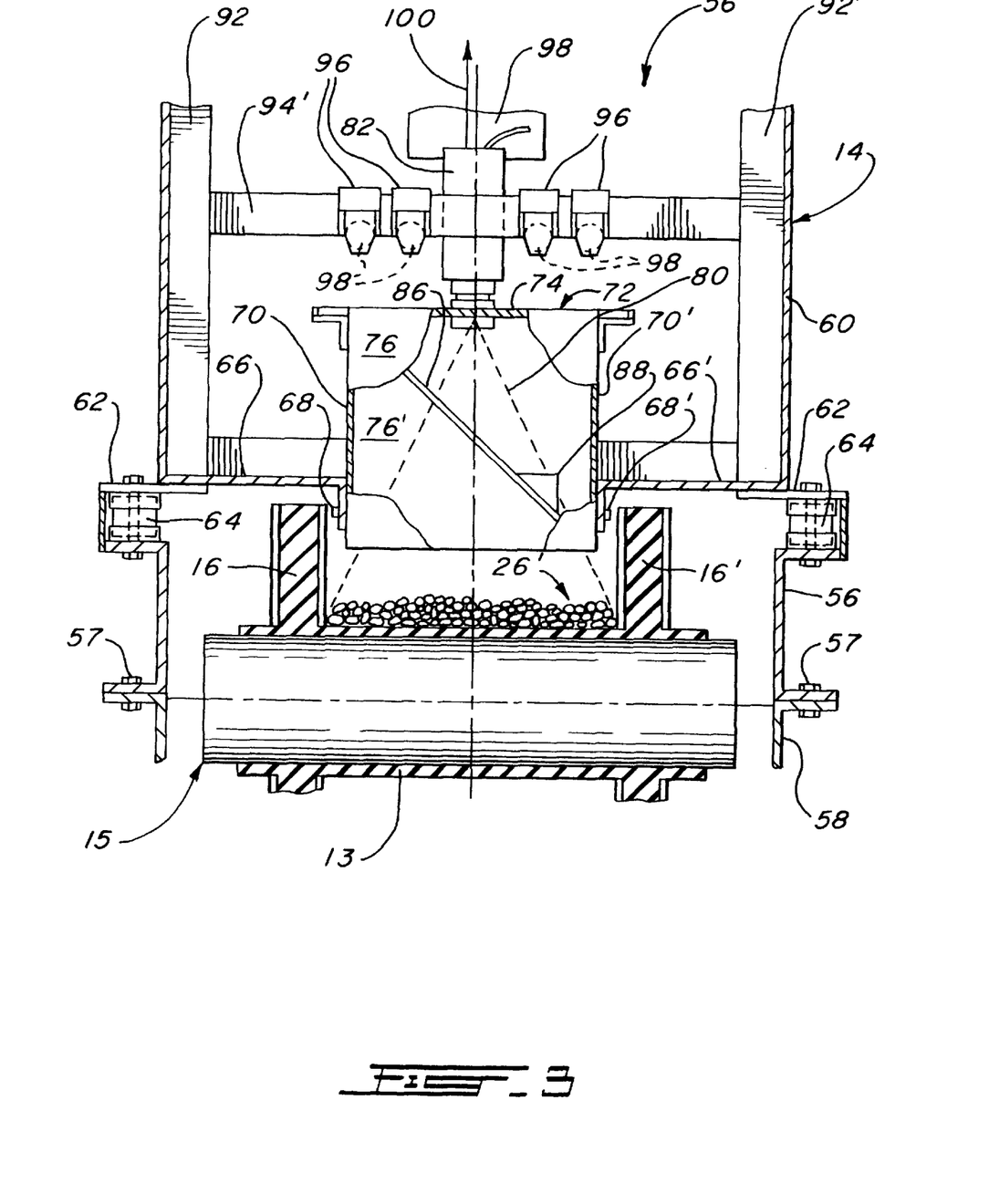
FIG. 3 is a partial cross-sectional end view along section line 3—3 of FIG. 2, showing the internal components of the inspecting station.

Turning now to FIGS. 2 and 3, internal components of the inspection station 12 will be now described. The enclosure 14 is formed of a lower part 56 for containing the conveyor 15 and being rigidly secured to a base 58 with bolt assemblies 57, and an upper part 60 for containing the optical components of the station 12 and being removably disposed on supporting flanges 62 rigidly secured to upper edge of the lower part 56 with bolted profile assemblies 64. At the folded ends of a pair of opposed inwardly extending flanged portions 66 and 66' of the upper part are secured through bolts 68 and 68' side walls 70 and 70' of a shield 72 further having top 74, front wall 76 and rear wall 76' to optically isolate the field of view 80 of a camera 82 for optically covering superficial wood chips 26' included in a representative portion of the inspected wood chips batch and being disposed within an inspection area. The camera 82 is located over the shield 72 and has an objective downwardly extending through an opening 84 provided on the shield top 74, as better shown in FIG. 2. Superficial wood chips 26' are distributed onto the conveyor belt 13 to present light reflection characteristics which are substantially representative of the wood chips 26 of the inspected batch. The camera 82 is used to sense light reflected on superficial wood chips 26' to produce electrical signals representing reflection intensity values for the superficial wood chips 26'. For the example described herein, although any appropriate monochrome camera could be used to provided detection of desired optical characteristics, a color RGB CCD video camera is preferably used to further provide color displaying capability for the operator. Diagonally disposed within shield 72 is a transparent glass sheet acting as a support for a calibrating reference support 88 as better shown in FIG. 3, whose function will be explained later in more detail. A shown in FIG. 2, the camera 82 is secured according to an appropriate vertical alignment on a central transverse member 90 supported at opposed end thereof to a pair of opposed vertical frame members 92 and 92' secured at lower ends thereof on flanged portions 66 and 66' as shown in FIG. 3. Also supported on the vertical frame members 92 and 92' are front and rear transverse members 94 and 94'. Transverse members 90, 94 and 94' are adapted to receive elongate electrical light units 96 which use standard fluorescent tubes 98 in the example shown, to direct light substantially evenly onto the inspected batch portion of superficial wood chips 26'. The camera 82 and light units 96 are powered via a dual output electrical power supply unit 98. Electrical image signal is generated by the camera 82 through output line 100. When used in cold environment, the enclosure 14 is preferably provided with a heating unit (not shown) to maintain the inner temperature at a level ensuring normal operation of the camera 82.

Referring to FIG. 2, an optional moisture sensing unit 78 is shown which is preferably disposed near the inspection station 12. The sensing unit 78 is used to inspect batches of material exhibiting variations in the moisture content, either between the batches or within any specific batch, which variations may affect reflectance characteristics of the superficial wood chips 26', thereby affecting reflection intensity values as measured by the camera 82. The moisture sensing unit 78 is preferably a non-contact sensing device such as the near-infrared sensor MM55plus supplied by NDC Infrared Engineering, Irwindale Calif. The unit 78 generates at an output 79 thereof electrical signals representing average moisture values for the superficial wood chips 26'.

Figure 4:
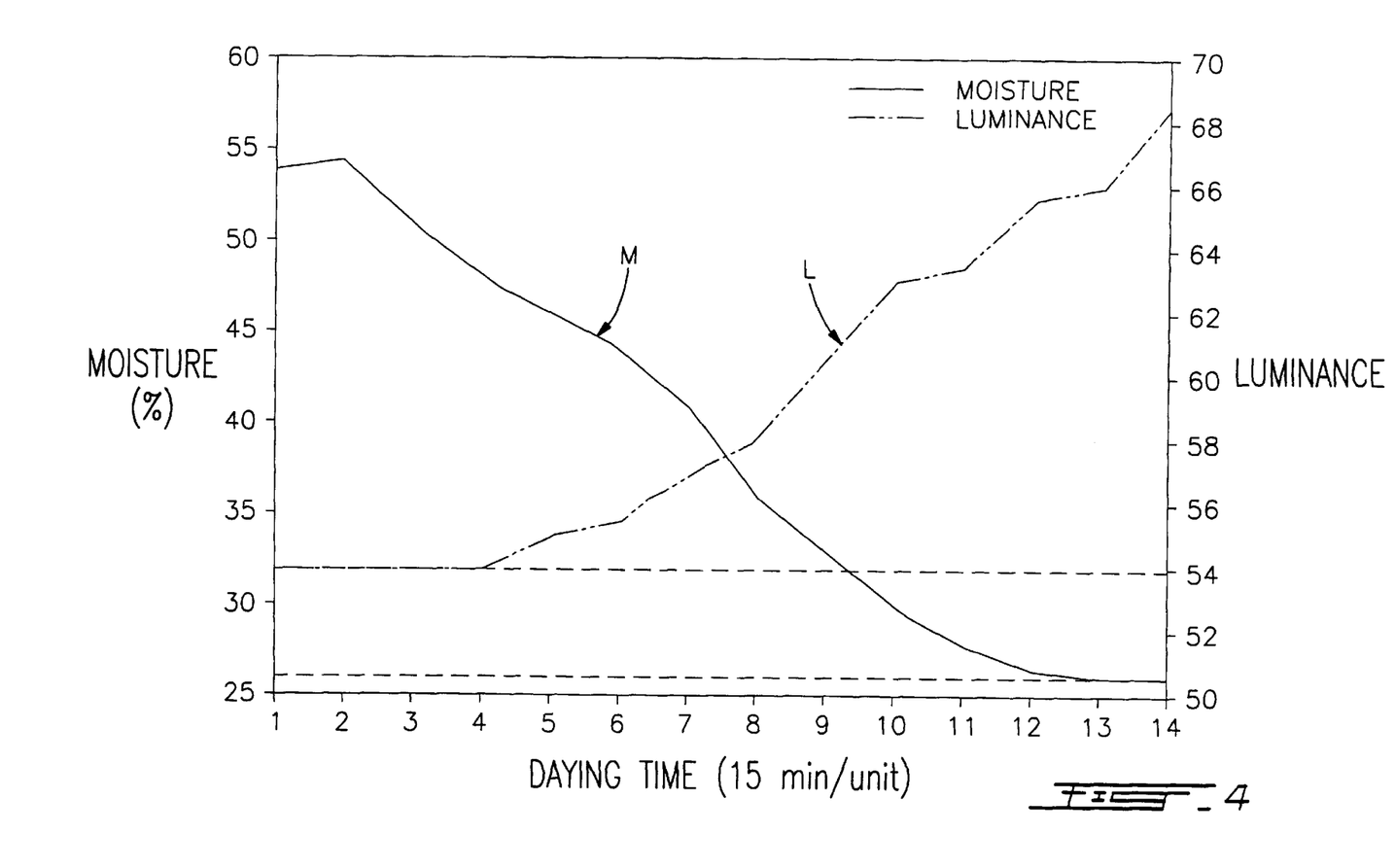
FIG. 4 is a graph showing the inverse relationship between moisture level and luminance level as measured on a sample of wood chips in term of drying time.

For example, while batches of wood chips stored in large containers before processing generally exhibit substantially uniform and stable moisture contents, chips batches stored in open sites may present moisture variations which may have a material effect on the reflectance measurements. In processes where high classification accuracy is required, consideration of the effect of moisture variations may be needed. Referring to FIG. 4, the overall inverse relationship between moisture level in percentage and luminance as periodically measured during drying of a sample of wood chips is illustrated, which relation may be roughly expressed by $\Delta l \approx -k\Delta m$, wherein $\Delta m$ represents any deviation in moisture value, $\Delta l$ represents a corresponding variation in luminance value, k being a scale constant having a positive real value. It can be seen that chips showing an initial moisture content of 54% as shown by curve M intersecting the left vertical axis, are roughly 27% brighter (passing from 54 to 68.5 in luminance as shown by curve L intersecting the right vertical axis) after their moisture was reduced to 26% after drying. That shift in measured luminance may be compensated by normalizing the reflection intensity values according to corresponding moisture deviations from a predetermined reference moisture value, as will be later explained in more detail.

Control and processing elements of the apparatus 10 will be now described with reference to FIG. 2. The apparatus 10 further comprises a computer unit 102 having an image acquisition module 104 coupled to line 100 for receiving image electrical signals from the camera 82, which module 104 could be any appropriate RGB image data acquisition electronic card currently available on the marketplace. The computer 102 is provided with an external communication unit 103 being coupled for bi-directional communication through lines 106 and 106' to a conventional programmable logic controller (PLC) 107 for controlling operation of the sample screw drive 28 and conveyor drive 18 through lines 108 and 110 respectively according to a predetermined program. The PLC 107 receives from line 112 batch data entered via an input device 114 by an operator in charge of batch registration and dumping operations, as will be explained later in more detail. The input device 114 is connected through a further line 116 to an image processing and communication software module 118 outputting control data for PLC through line 119 while receiving acquired image data and PLC data through lines 120 and 122, respectively. The image processing and communication module 118 receives input data from a computer data input device 124, such as a computer keyboard, through an operator interface software module 126 and lines 128 and 130, while generating image output data toward a display device 132 through operator interface module 126 and lines 134 and 136. Where a moisture sensing unit 78 is provided, the module 118 also receives the moisture indicating electrical signals through a line 81.

Figure 5:
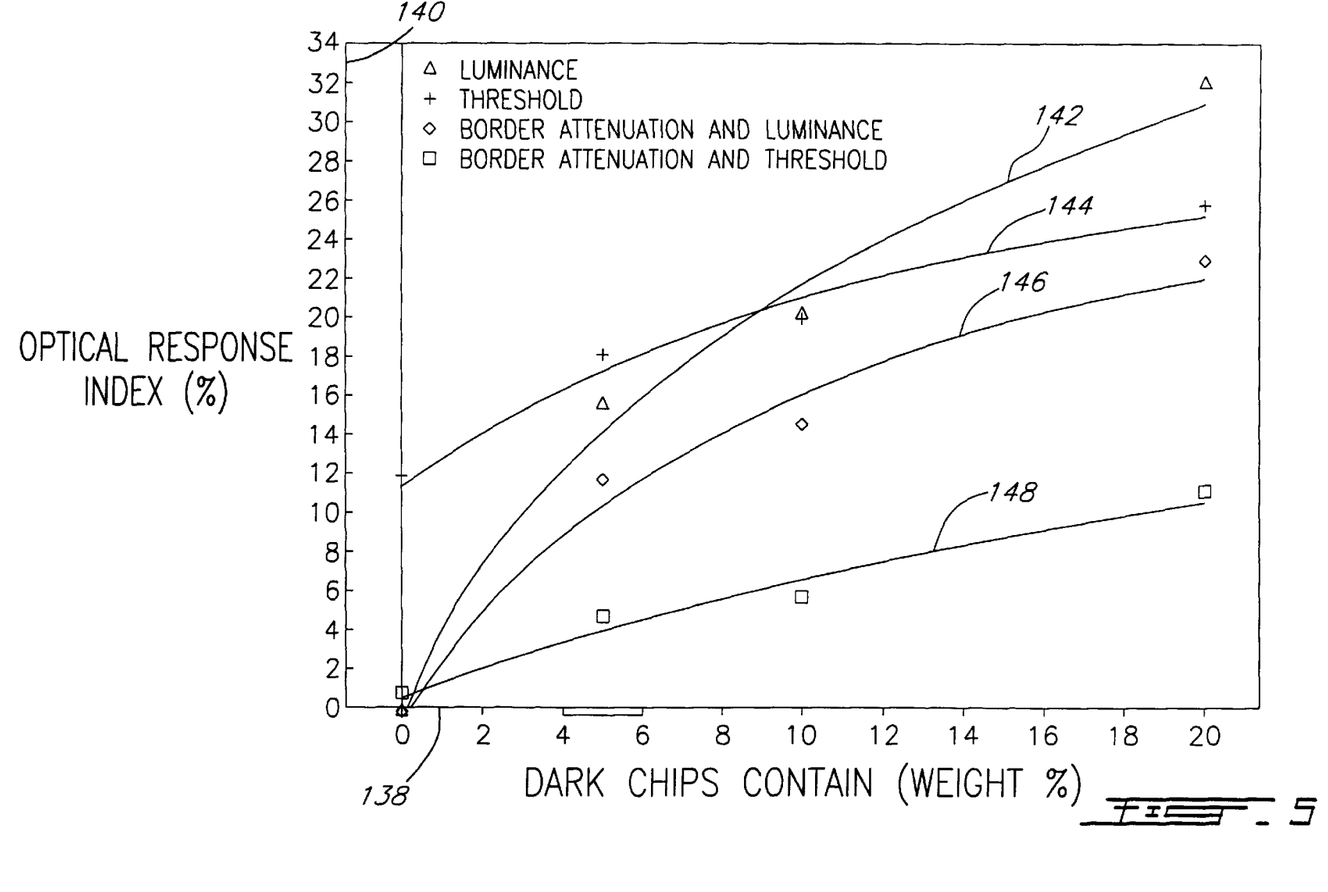
FIG. 5 is a graph showing a set of curves representing general relations between measured optical characteristics and dark wood chips contain associated with several samples.

Turning now to FIG. 5, general relations between measured optical characteristics and dark wood chips contain associated with several samples are illustrated by the curves traced on the graph shown, whose first axis 138 represents dark chips contain by weight percentage characterizing the sample, and whose second axis 140 represents corresponding optical response index measured. In the example shown, four curves 142, 144, 146, and 148 have been fitted on the basis of average optical response measurements for four (4) groups of wood chips samples prepared to respectively present four (4) distinct dark chips contains by weight percentage, namely 0% (reference group), 5%, 10% and 20%. Measurements were made using a RGB color camera coupled to an image acquisition module connected with a computer, as described before. To obtain curves 142 and 146, luminance signal values derived from the RGB signals corresponding to all considered pixels were used to derive an optical response index which is indicative of the relative optical reflection characteristic of each sample. As to curve 142, mean optical response index was obtained according to the following ratio:

$$I = \frac{L_R}{L_S} - 1$$

Wherein I is the optical response index, $L_R$ is a mean luminance value associated with the reference samples and $L_S$ is a mean luminance value based on all considered pixels associated with a given sample. Curve 146 was obtained through computer image processing to attenuate chip border shaded area which may not be representative of actual optical characteristics of the whole chip surface. To obtain curves 144 and 148, reflection intensity of red component of RGB signal was compared to a predetermined threshold to derive the optical response index according the following relation:

$$I = \frac{P_D}{P_T}$$

wherein I is the optical response index, $P_D$ is the number of pixels whose associated red component intensity is found to be lower than the predetermined ratio (therefore indicating a dark pixel) and $P_T$ is the total number of pixels considered. As for curve 146, curve 148 was obtained through computer image processing to attenuate chip border shaded areas. It can be seen from all curves 142, 144, 146, and 148 that the optical response index grows as dark chip contains increases. Although curve 148 shows the best linear relationship, experience has shown that all of the above described calculation methods for the optical response index can be applied, provided reference reflection intensity data are properly determined, as will be explained later in more detail.

Returning now to FIGS. 1, 2 and 5, operation of the method and apparatus according to the preferred embodiment of the present invention will be now explained. Referring to FIG. 2, before starting operation, the apparatus 10 must be initialized through the operator interface module 126 by firstly setting system configuration. Camera related parameters can be then set through the image processing and communication module 118, according to the camera specifications. The initialization is completed by camera and image processing calibration through the operator interface module 126.

System configuration provides initialization of parameters such as data storage allocation, image data rates, communication between computer unit 102 and PLC 107, data file management, wood type identification and corresponding reference threshold levels setting. As to data storage allocation, images and related data can be selectively stored on a local memory support or any shared memory device available on a network to which the computer unit 102 is connected. Directory structure is provided for software modules, system status message file, current accepted batch data, current rejected batch data and recorded rejected batch data. Image rate data configuration allows to select total number of acquired images for each batch, number of images to be stored amongst the acquired images and acquisition rate, i.e. period of time between acquisition of two successive images. Therefore, to limit computer memory requirements, while a high number of images can be acquired for statistical purposes, only a part of these images, particularly regarding rejected batches, need to be stored. The PLC configuration relates to parameters governing communication between computer unit 102 and PLC 107, such as master-slave protocol setting (ex. DDE), memory addresses for a) batch data input synchronization for batch presence checking following dumping information; b) alarm set for indicating a rejected batch; and c) <<heart beat>> for indication of system interruption, <<heart beat>> rate and batch presence monitoring rate. Data file management configuration relates to parameters regarding batch input data, statistical data for inspected batches, data keeping period before deletion for acceptable batch and data keeping checking rate. Statistical data file can typically contain information relating to batch number, supplier contract number, wood type, mean intensity values for Red, Green and Blue (RGB) signals, mean luminance, date of acquisition, batch status (acceptable or rejected). Data being systematically updated on a cumulative basis, the statistical data file can be either deleted or recorded as desired by the operator to allow acquisition of new data.

All desired wood types can be identified as well as associated reference threshold levels used as reference reflectance intensity data. For a given wood type, based on initial visual inspection by the operator of optical characteristics presented by several representative samples for that particular wood type, the operator sets a low threshold value under which an inspected batch shall be rejected as containing an unacceptable amount of dark chips for that type of wood. It is to be understood that batch containing chips blend of known wood types can be characterized in a same way. In addition to visual inspection, process parameters such as required quantity of bleaching agent, processing time or spent energy measured for prior inspected batches can be recorded to find out low threshold value associated with minimum processing yield required to qualify a batch acceptable. Preferably, reference reflection intensity data may include range threshold data delimiting a plurality of wood chips grades. In that case, the operator may also set a maximum threshold value above which an inspected batch could be considered more than acceptable for that particular grade, ex. grade 1, and therefore could be classified in a higher quality grade of wood chips, ex. grade 2. The current levels setting for a current batch can be modified, stored or deleted as desired by the operator. It is to be understood that specific values given to the classification thresholds are also dependent upon calibration performed. Once the camera 82 is being configured as specified, calibration of the camera and the image processing module can be carried out by the operator through the operator interface, to ensure substantially stable light reflection intensities measurements as a function of time even with undesired lightning variation due to temperature variation and/or light source aging, and to account for spatial irregularities inherent to CCD's forming the camera sensors. Calibration procedure first consists of acquiring <<dark>> image signals while obstructing with a cap the objective of the camera 82 for the purpose of providing offset calibration, and acquiring <<lighting>> image signals with a gray target presenting uniform reflection characteristics being disposed within the inspecting area on the conveyer belt 13 for the purpose of providing spatial calibration. Calibration procedure then follows by acquiring image signals with an absolute reference color target, such as a color chart supplied by Macbeth Inc., to permanently obtain a same measured intensity for substantially identically colored wood chips, while providing appropriate RGB balance for reliable color reproduction. Initial calibration ends with acquiring image signals with a relative reference color target permanently disposed on the calibrating reference support 88, to provide an initial calibration setting which account for current optical condition under which the camera 82 is required to operate. Such initial calibration setting will be used to perform calibration update during operation, as will be later explained in more detail.

Where a moisture sensing unit 78 is provided, further calibration steps are carried out, using a chips sample which is subjected to a progressive drying process according to an experimental moisture range that is representative of the actual moisture range, to derive a reference moisture curve through standard measurement in laboratory, such as the curve M shown in FIG. 4. The moisture curve is then compared with a reference moisture curve obtained with the sensing unit 78, allowing an initial calibration thereof. While the chips sample is being dried, luminance values are also measured to derive a luminance curve associated with the obtained moisture curve, such as curve L shown in FIG.4. Then, luminance compensation values to be used for the normalization to the predetermined reference moisture value can be obtained through the relation $\Delta l \approx -k \Delta m$, with $\Delta m = m_c - m_r$, wherein $m_c$ is a current moisture value as measured by the unit 78 and $m_r$ is the predetermined reference moisture value.

Initialization procedure being completed, the apparatus 10 is ready to operate, the computer unit 102 being in permanent communication with the PLC 107 to monitor the operation of the screw drive 28 indicating the presence of a new batch to be inspected. Whenever a new batch is detected, the following sequence of steps are performed: 1) end of PLC monitoring; 2) batch data file reading (type of wood chips, batch identification number); 3) image acquisition and processing for wood chips batch classification according to the set threshold values; and 4) data and image recording after batch inspection.

Image acquisition consists in sensing light reflected on the superficial wood chips 26' included in the present batch portion to produce electrical signals representing reflection intensity values for the superficial wood chips 26', forming an image thereof Although a single batch portion of superficial chips covered by camera field of view 80 may be considered to be representative of optical characteristics of a substantially homogeneous batch, wood chips batches being known to be generally heterogeneous, it is preferable to consider a plurality of batch portions by acquiring a plurality of corresponding image frames of electrical pixel signals. In that case, image acquisition step is repeatedly performed as the superficial wood chips of batch portions are successively transported through the inspection area defined by the camera field of view 80. Where a moisture sensing unit 78 is provided, superficial wood chips 26' are scanned by infrared beam generated by the unit 78 which analyze reflected radiation to generate the moisture indication signals. It is to be understood that while the moisture sensing unit 78 is disposed at the output of the inspection station 12 in the illustrated embodiment, other locations downstream or upstream to the inspection station 12 may be suitable.

As to image processing, the image processing and communication unit 118 is used to derive from the acquired pixel signals global reflection intensity data for the inspected batch, designated before as optical response index with reference to FIG. 5. Calibration updating of the acquired pixel signals is performed considering pixels signals corresponding to the relative reference target as compared with the initial calibration setting, to account for any change affecting current optical condition. Then, image noise due to chip border shaded areas, snow and/or ice and visible belt areas are preferably filtered out of the image signals using known image processing techniques. Where a moisture sensing unit 78 is provided, the image processing and communication unit 118 applies compensation to the acquired pixel signals using the corresponding moisture indicating electrical signals.

Global reflection intensity data may then be derived by averaging reflection intensity values represented by ether all or representative ones of the acquired pixel signals for the batch portions considered, to obtain mean reflection intensity data. Alternately, the global reflection intensity data may be derived by computing a ratio between the number of pixel signals representing reflection intensity values above a predetermined threshold value and the total number of pixel signals considered. Any other appropriate derivation method known in the art could be used to obtain the global reflection intensity data from the acquired signals. Optionally, the global reflection intensity data may include standard deviation data, obtained through well known statistical methods, variation of which may be monitored to detect any abnormal heterogeneity associated with an inspected batch.

As to wood chips batch classification, the image processing and communication unit 118 compares the global reflection intensity data to reference reflection intensity data including range thresholds, to provide classification of the inspected wood chips batch into a proper wood chip grade according its light reflection characteristics. As mentioned before, reference reflection intensity data may comprise threshold data respectively corresponding to a plurality of wood chip types. In that case, batch data input device 114 sends to the image processing and communication an electrical signal indicating a specific one of wood types to which the wood chips of the current inspected batch correspond, and classification is performed by comparing the global reflection intensity data to the reference reflection intensity data corresponding to the specific wood chips type accordingly. Alternately, input device 114 can be in the form of an automated reading device capable of detecting machine readable code associated with the inspected batch, the code representing the corresponding one of chips wood type. In a case where the inspected batch is classified as being acceptable for a given grade, the computer unit 102 resumes PLC monitoring for a next batch to be inspected. Otherwise, whenever an unacceptable batch is detected and therefore rejected, the computer unit causes an alarm to be set by the PLC before resuming PLC monitoring. In operation, the computer unit 102 continuously sends a normal status signal in the form of a <<heart beat>> to the PLC through line 106'. The computer unit 102 also permanently monitors system operation in order to detect any software and/or hardware based error which could arise to command inspection interruption accordingly. Preferably, to save computer memory, the computer unit 102 does not keep all acquired images, so that alter a predetermined period of time, images of acceptable inspected batches are deleted while images of rejected batches are recorded for later use. The image processing and communication module 118 performs system status monitoring functions such as automatic interruption conditions, communication with PLC, batch image data file management, dumping monitoring and monitoring status. These functions result in messages generation addressed to the operator through display 132 whenever appropriate action of the operator is required. For automatic interruption conditions, such a message may indicate that video (imaging) memory initialization failed, an illumination problem arose or a problem occurred with the camera 82 or the acquisition card. For PLC communication, the message may indicate a failure to establish communication with PLC 107, a faulty communication interruption, communication of a <<heart beat>> to the PLC 107, starting or interruption of the <<heart beat>>. As to batch data files management, the message may set forth that acquisition initialization failed, memory storing of image or data failed, a file transfer error occurred, monitoring of recorded is being started or ended. As to chips dumping monitoring, the message may alert the operator that batch data has not been properly read, dumping monitoring being started or ended. Finally, general operation status information is given to the operator through messages indicating that the apparatus is ready to operate, acquisition has started, acquisition is in progress, image acquisition is completed and alarm for rejected batch occurred.

Figure 6:
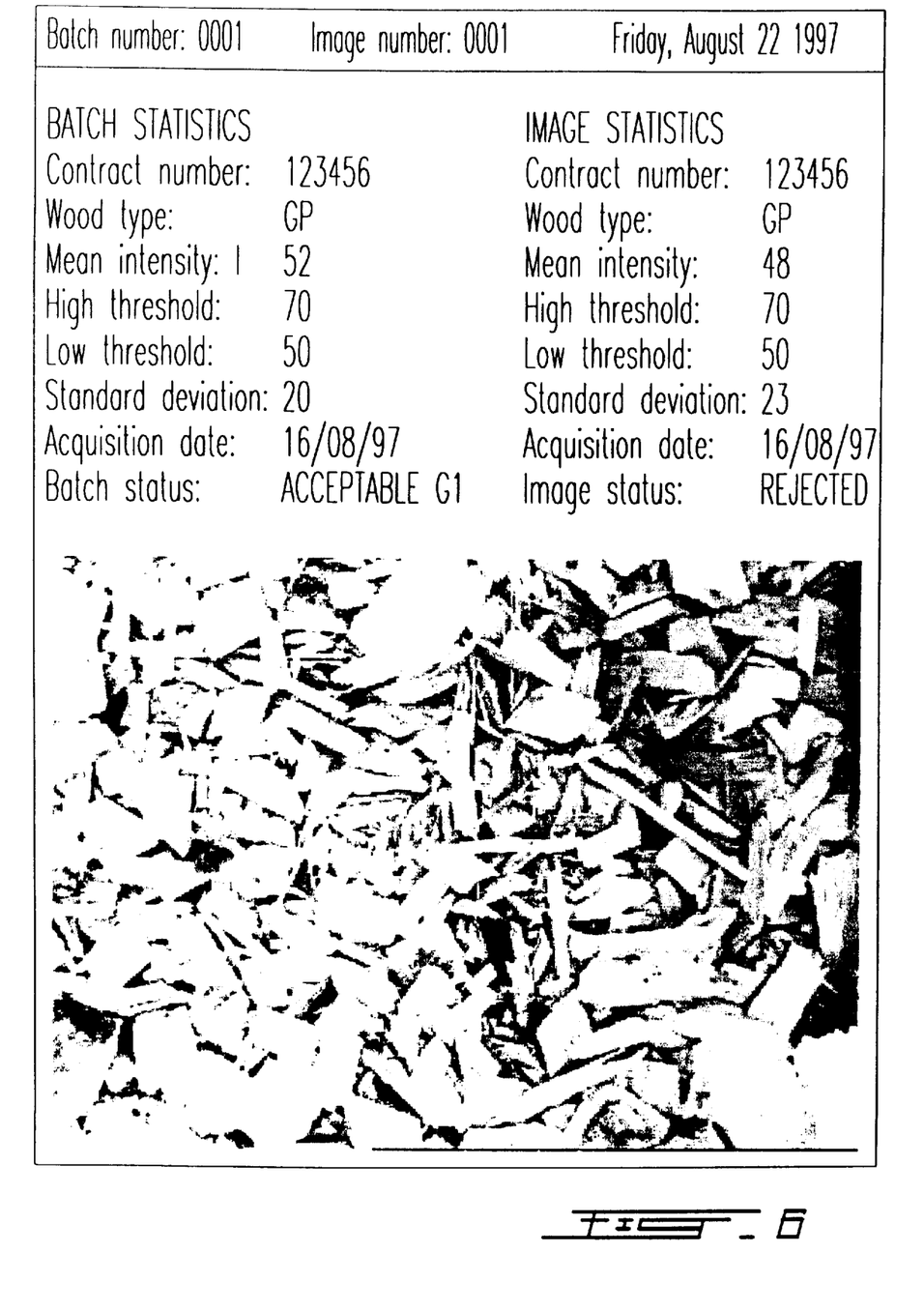
FIG. 6 is an example of a output data report and image displayed which can be obtained using the method and apparatus according to the present invention.

Referring now to FIG. 6, a typical data output report which can be obtained using the above described method and apparatus is illustrated, which reports presents statistics associated with a selected wood chips image shown, as well as statistics related to the corresponding batch of gray pine wood chips. It can be seen from image statistics shown that although status of the current image indicates that it has been rejected with a mean intensity value of 48 as compared to a low threshold value set to 50, the corresponding cumulative batch data in turn indicate with a mean intensity of 52 that the batch as whole is qualified as acceptable for grade 1, while being not qualified as grade 2 for being lower than the high threshold set to 70.

It is within the ambit of the present invention to cover any obvious modification of the described embodiment of the method and apparatus according to the present invention, provided it falls within the scope of the appended claims.

We claim:

1. An apparatus for classifying batches of wood chips according to light reflection characteristics comprising:

illumination means for directing substantially even light onto an area of wood chips included in at least a representative portion of an inspected one of said wood chips batches, said illuminated wood chips presenting light reflection characteristics being substantially representative of the wood chips of the inspected batch;

image creating means for sensing light reflected on the illuminated area of wood chips included in said batch portion to produce first electrical signals representing reflection intensity values for the wood chips included in said batch portion;

moisture detector means for producing second electrical signals representing average moisture values for the illuminated wood chips included in said batch portion;

means for deriving from said first and second electrical signals global reflection intensity data for the inspected batch, said global reflection intensity data being normalized according to a predetermined moisture reference value; and means for comparing the global reflection intensity data with reference reflection intensity data to provide classification of said inspected batch of wood chips according its light reflection characteristics, said classification enabling adjustment of process parameters of a pulp production process to be fed with the inspected batch.

2. An apparatus according to claim 1, wherein said reference reflection intensity data include range threshold data delimiting a plurality of wood chips grades to provide said classification accordingly.

3. An apparatus according to claim 2, further comprising an operator interfacing unit provided with a display means for reproducing created image from said image electrical signals, said unit being provided with data entry means allowing an operator to adjust said range threshold data corresponding to said plurality of wood chips grades for the purpose of said classification.

4. An apparatus according to claim 1, wherein said reference reflection intensity data comprise data respectively corresponding to a plurality of wood chip types, said apparatus further comprising means for generating an electrical signal indicating a specific one of said types to which said wood chips correspond, said data comparing means using said reference reflection intensity data corresponding to said specific one of said wood chips types to provide said classification.

5. An apparatus according to claim 4, wherein said electrical signal generating means is a data input device allowing an operator to select said specific one of said types of wood chips corresponding to said inspected batch.

6. An apparatus according to claim 4, wherein said electrical signal generating means is an automated reading device capable of detecting machine readable code associated with said inspected batch, said code representing said specific one of said types of wood chips corresponding to the inspected batch.

7. An apparatus according to claim 1, wherein said global reflection intensity data include mean reflection intensity data, said deriving means averaging said reflection intensity values to produce said mean reflection intensity data.

8. An apparatus according to claim 7, wherein said global reflection intensity data further include standard deviation generated by said deriving means from said reflection intensity values.

9. An apparatus according to claim 7 or 8, wherein said deriving means calibrate and filter said reflection intensities values to be used for deriving said global reflection intensity data.

10. An apparatus according to claim 1, wherein electrical signals deriving means compute a ratio between a number of said electrical signals representing reflection intensity values above a predetermined threshold value and a total number of said electrical signals to produce said global reflection intensity data.

11. An apparatus according to claim 1, further comprising conveyor means for transporting said batch portion of superficial wood chips through an inspection area associated with said illumination means and said image creating means.

12. An apparatus according to claim 11, wherein there being a plurality of said representative batch portions including wood chips, said illumination means repeatedly directing light onto respective superficial wood chips of said batch portions while said image creating means repeatedly sense light reflected on the illuminated wood chips of said batch portions to produce said image electrical signals representing reflection intensity values for the wood chips of said batch portions.

13. An apparatus according to claim 12, further comprising hopper means for receiving said inspected wood chips batch and means coupled to said hopper means for successively sampling said inspected batch portions prior to being transported through said inspection area.

14. An apparatus according to claim 1, wherein said detector means comprise an infrared detector.

15. A method for classifying batches of wood chips according to light reflection characteristics comprising the steps of:

a) directing substantially even light onto an area of wood chips included in at least a portion of an inspected one of said wood chips batches, said illuminated wood chips presenting light reflection characteristics being substantially representative of the wood chips of the inspected batch;

b) sensing light reflected on the illuminated area of wood chips included in said batch portion to produce first electrical signals representing reflection intensity values for the wood chips included in said batch portion;

c) measuring moisture of said illuminated wood chips to produce second electrical signals representing average moisture values for the illuminated wood chips included in said batch portion;

d) deriving from said first and second electrical signals global reflection intensity data characterizing the inspected batch of wood chips, said global reflection intensity data being normalized according to a predetermined moisture reference value; and e) comparing the global reflection intensity data with reference reflection intensity data to provide classification of said inspected batch of wood chips according its light reflection characteristics, said classification enabling adjustment of process parameters of a pulp production process to be fed with the inspected batch.

16. A method according to claim 15, wherein said reference reflection intensity data include range threshold data delimiting a plurality of wood chips grades to provide said classification accordingly.

17. A method according to claim 15, wherein said reference reflection intensity data correspond to a plurality of wood chip types, said method further comprising between said steps d) and e) a step of: i) providing an electrical signal indicating a specific one of said types to which said wood chips corresponds and wherein said step e) is performed by comparing said global reflection intensity data to said reference reflection intensity data corresponding to said specific one of said wood chips types.

18. A method according to claim 15, wherein said global reflection intensity data include mean reflection intensity data derived by averaging said reflection intensity values.

19. A method according to claim 18, wherein said global reflection intensity data further include standard deviation reflection intensity data derived from said reflection intensity values.

20. A method according to claim 18 or 19, wherein said reflection intensities values are being calibrated and filtered prior to be used for deriving said global reflection intensity data.

21. A method according to claim 15, wherein said global reflection intensity data are derived by computing a ratio between a number of said electrical signals representing reflection intensity values above a predetermined threshold value and a total number of said electrical signals.

22. A method according to claim 15, wherein there being a plurality of said representative batch portions including superficial wood chips, said steps a) b) and c) being repeatedly performed for said batch portions to derive said global reflection intensity data at said step d).

23. A method according to claim 22, wherein said steps a) b) and c) are repeatedly performed while said batch portions including illuminated wood chips are successively transported through an inspection area.

24. A method according to claim 23, wherein said batch portions including illuminated wood chips are successively sampled from said inspected batch prior to being transported through said inspection area.

* * * * *